United States Patent [19]

Lucci

[11] Patent Number: 4,556,518

[45] Date of Patent: Dec. 3, 1985

[54] PREPARATION OF 13-CIS RETINOIC ACID

[75] Inventor: Robert Lucci, Wickoff, N.J.

[73] Assignee: Hoffmann-La Roche Inc., Nutley, N.J.

[21] Appl. No.: 631,374

[22] Filed: Jul. 16, 1984

Related U.S. Application Data

[62] Division of Ser. No. 448,660, Dec. 10, 1982, abandoned.

[51] Int. Cl.[4] ................... C07C 51/353; C11C 1/00
[52] U.S. Cl. .................................................. 260/413
[58] Field of Search ................................. 260/413 L

[56] References Cited

U.S. PATENT DOCUMENTS 4,051,174  9/1977  Stoller et al. ................... 260/413 L

OTHER PUBLICATIONS

Pattendon et al., "J. Chem. Soc." (C) (1968), pp. 1984–1997.

*Primary Examiner*—J. E. Evans
*Attorney, Agent, or Firm*—Jon S. Saxe; George M. Gould; William H. Epstein

[57] ABSTRACT

A new process for producing 13-cis retinoic acid in high yields from the reaction product of a butenolide and a Wittig salt.

14 Claims, No Drawings

PREPARATION OF 13-CIS RETINOIC ACID

This is a division of application Ser. No. 448,660 filed Dec. 10, 1982, now abandoned.

BACKGROUND OF INVENTION

The isomer of Vitamin A acid, 13-cis Vitamin A acid has become a valuable pharmaceutical due to its use in treating acne. However, this isomer has been very difficult to produce. Pattenden and Weedon, J. Chem. Soc. (C), 1984–1997 [ ] 968] have disclosed a procedure for preparing 13-cis Vitamin A acid by reacting a $C_{15}$-Wittig salt, i.e. [3-methyl-5-(2,6,6-trimethyl-1-cyclohexen-1-yl)-2,4-pentadienyl]-triphenyl phosphonium salt and a $C_5$-butenolide, i.e. 5-hydroxy-4-methyl-2-5[H]-furanone to produce a mixture of the cis isomers of retinoic acids. This process suffered from the drawback that the yield of the mixture of cis isomers of retinoic acid was poor. Furthermore, it has been difficult to convert by isomerization this mixture of isomers into the specific isomer 13-cis retinoic acid. This is especially true since the isomers produced by this process contain a cis configuration about both the 11- and 13-positions. It has been very difficult to selectively isomerize the 11-cis double bond without isomerizing the 13-cis double bond. Many of the isomerization techniques used have been relatively ineffective in selectively isomerizing the 11-cis double bond without affecting the 13-cis double bond. Any isomerization of the 13-cis double bond reduces the yield of the 13-cis Vitamin A acid.

Therefore, it has been desired to provide a process where the various cis isomers are produced by the Wittig reaction in high yields and the cis isomers are selectively isomerized without affecting the 13-cis double bond to obtain the 13-cis isomer of Vitamin A acid in high yields and in pure form.

SUMMARY OF INVENTION

In accordance with this invention, we have discovered that when a Wittig salt of the formula

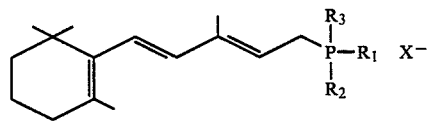

wherein $R_1$, $R_2$ and $R_3$ are aryl or di(lower alkyl) amino, and X is halogen
is reacted at a temperature of from $-10°$ C. to $-50°$ C. in a lower alkanol solvent in the presence of an alkali metal hydroxide with a butenolide of the formula

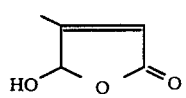

a mixture containing the 11,13 dicis isomer of retinoic acid which has the formula

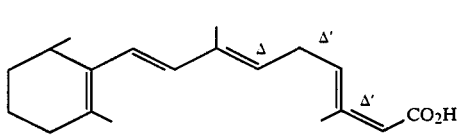

where the $\Delta$ indicates a trans configuration about the double bond; and $\Delta'$ indicates a cis configuration about the double bond;
and the 13-cis vitamin A acid which has the formula:

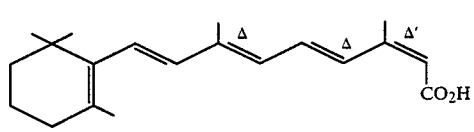

wherein $\Delta$ and $\Delta'$ are as above
is produced in high yields. In the next step for producing the 13-cis retinoic acid isomer of formula IV, the compound of formula III either isolated or in admixture with the compound of formula IV is converted in yields of over 90% to the compound of formula IV utilizing as a catalyst a compound or complex of palladium or rhodium wherein the catalyst is other than palladium or rhodium phthalocyanin or other than a compound or complex containing a cyanide ion. The preferred catalyst for use in this isomerism is a palladium compound formed by reacting palladium (II) nitrate with a tri(lower alkyl) or aryl phosphine and tri(lower alkyl)amine. By the use of this preferred catalyst, isomerization is carried out to produce the compound of formula IV almost instantaneously in high yields without any need for recycling.

DETAILED DESCRIPTION OF THE INVENTION

As used throughout this application, the term "lower alkyl" includes both straight chain and branched chain alkyl groups having from 1 to 7 carbon atoms, such as methyl, ethyl and propyl, preferably methyl. As used herein, the term "lower alkoxy" comprehends lower alkoxy groups having from 1 to 7 carbon atoms such as methoxy and ethoxy. As also used herein, the term "lower alkanoic acids" comprehends an alkanoic acid having from 2 to 7 carbon atoms such as acetic, butyric and propionic acid. As further used herein, the term "halogen" includes all halogens, unless otherwise stated, such as fluorine, chlorine, bromine and iodine.

As also used herein, the term "aryl" signifies the mononuclear aromatic hydrocarbon group phenyl, etc. which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be substituted with one or more of the aforementioned groups. The preferred aryl groups are the substituted and unsubstituted mononuclear aryl groups, particularly phenyl and tolyl.

In accordance with this invention, the Wittig salt of formula I is first reacted with the butenolide of formula II, via a Wittig reaction, to produce a mixture containing the compounds of formulae III and IV. This reaction is carried out utilizing the conditions of a Wittig reaction. While the compound of formula I can be any conventional Wittig salt, it is generally preferred that the compound of formula I is a triphenyl phosphonium chloride salt.

Furthermore, we have found that when the compounds of formulae I and II are reacted at temperatures of from −10° to −50° C., preferably from −20° C. to −50° C., with temperatures of from −30° C. to −45° C. being especially preferred, the mixture of the compounds of formulae III and IV is produced in yields of at least 90% and above. Furthermore, the use of these temperatures prevents formation of isomers of vitamin A acid other than the 13-cis or 11,13-dicis vitamin A acid.

In carrying out this reaction, a base and an inert organic solvent are generally utilized. The organic solvent is chosen so that it will not solidify at the low temperature utilized in carrying out the Wittig reaction. Therefore, the choice of a particular inert solvent will depend upon the temperature utilized to carry out the Wittig reaction. Among the preferred solvents are the lower alkanol solvents such as isopropanol, ethanol, methanol, with isopropanol being especially preferred. In accordance with this invention, the preferred bases are the alkali metal hydroxides such as potassium hydroxide, sodium hydroxide, lithium hydroxide. For best results in far as yield and quality of product is concerned, it is preferred to utilize potassium hydroxide and isopropanol. In carrying out this reaction, it is generally preferred to utilize an inert atmosphere, preferably nitrogen.

In accordance with this invention, the reaction of the compounds of formulae I and II produces a mixture of the compounds of formulae III and IV. If desired, this mixture can be directly converted to the compound of formula IV in the next step by isomerization without isolation of the compound of formula III from this mixture. On the other hand, if desired, the compound of formula III can be isolated from this mixture and converted into the compound of formula IV. If it is desired to separate this mixture into the compounds of formulae III and IV, any conventional isomeric separation technique can be utilized. Among the preferred methods is fractional crystallization.

In general, the Wittig reaction of the compounds of formulae II and III produces a mixture containing about 70 to about 90% of the 11,13-dicis-retinoic acid of formula III and about 10 to about 30% of the 13-cis isomer of formula IV. Furthermore, by utilizing low temperatures i.e. temperatures below −20° C. and preferably at −30° C. to −50° C., one obtains the mixture of the retinoic acids of formulae III and IV in a yield of at least 90%, based upon the butenolide of formula II used as the starting material.

In the next step of the process of this invention, either the compound of formula III or the mixture containing the compound of formulae III and IV produced from the reaction of the compound of formulae I and II can be isomerized to the pure compound of formula IV. This isomerization is carried out by treating the compound of formula III in an inert solvent medium utilizing as a catalyst a compound or complex of palladium or rhodium wherein the catalyst is other than palladium or rhodium phthalocyanin or other than a compound or complex having a cyanide ion. Generally, this reaction is carried out a temperature of 10° C. to 150° C. with temperatures of from 40° C. to 65° C. being preferred and temperatures of 45° C. to 55° C. being especially preferred.

In accordance with the present invention, isomerization of the compound of formula III can be carried out by utilizing any compound or complex of palladium or rhodium other than palladium phtalocyanin, rhodium phthalocyanin, and complexes or compounds containing a cyanide ion. In accordance with this invention, it has been found that these catalysts selectively isomerize the 11-cis double bond to the corresponding trans double bond without affecting the 13-cis double. While some of the compounds or complexes of rhodium or palladium may not provide the 13-cis compound of formula IV in high yields, the fact that they only selectively isomerize the 11-cis double bond is of extreme importance. In such cases, the yields may be improved by recycling the unconverted 11,13-cis compound of formula IV and subjecting this compound once again to isomerization. If the catalyst would have isomerized the 13-cis to a 13-trans double bond in any amount, then there would have been a loss of yield. This is true since the 13-trans double bond cannot be easily isomerized. Furthermore, that these catalysts do not in any way effect the 13-cis bond allows the isomerization to take place without the need for isolating the 13-cis isomers of formula IV from the reaction product of the Wittig reaction. In this manner, the reaction product of the isomerization reaction may be repeatedly subjected to the catalytic isomerization to improve the yield without isolation of the compound of formula IV.

Any of the compounds or complexes of palladium as disclosed in U.S. Pat. No. 4,051,174, Sept. 27, 1977, Stoller et al., may be utilized in accordance with this invention. While it is preferred that the catalytic system be homogenous, a heterogenous catalytic system can also be used. In the case of a heterogeneous catalytic isomerization, the catalyst can be used in the absence of a carrier material or it can be supported on a carrier material. The carrier material can be any of the customary carrier materials such as, for example, carbon, nickel oxide, aluminium oxide, barium sulphate, calcium carbonate, molecular sieves and the like. Certain polymers such as Nylon, Perlon and the like can also be used as the carrier material. The catalyst can be brought onto the carrier materials by conventional procedure.

The palladium or rhodium compounds or complexes which are used as catalysts in this invention are preferably salts or complexes of palladium or rhodium. Among the palladium salts or complexes which can be utilized are the following: $PdCl_2$, $PdBr_2$, $PdF_2$, $PdI_2$, $K_2PdCl_4$, $PdSO_4$, $K_2PdBr_4$, $(CH_3CN)_2PdCl_2$, $Pd(OAC)_2$, (benzonitrile)$_2PdCl_2$, (benzonitrile)$_2PdBr_2$, $(C_3H_5PdCl)_2$, (cyclohexene-$PdCl_2$)$_2$, (1,5-cyclooctadiene)$PdCl_2$, (1,5-cyclooctadiene)$PdBr_2$, (1,5-cyclooctadiene)$PdI_2$, (cyclooctatetraene)$PdBr_2$, (acrylonitrile)$_2PdCl_2$, $Pd(NO_3)_4(NH_4)_2$, $Pd(pyridine)_2$-$((NO_2)_2$, $[N(CH_2)_3$benzyl]$_2Pd(NO_2)_4$, $Pd(NH_3)_2Cl_2$, $Pd(NH_3)_2(NO_2)_2$, $Pd(2,2$-bipyridyl)$Cl_2$, $(NH_4)_2PdCl_4$, $(NH_4)_2PdCl_6$, $PdS_2$, $K_2PdCl_6$, (ethylenediamine)$Pd(NO_2)_3$, (amylamine)$_2Pd(NO_2)_2$, $(NH_3)_4Pd(NO_3)_2$, $Pd(salicylaldoxime)_2$, succinic acid dinitrile)$PdCl_2$, (cyclooctatetraene)$PdCl_2$, (azeobenzene)$_2PdCl_2$, (bipyridyl)$Pd(NO_2)_2$, $K_2Pd(malonate)_2$, (tricyclohexylphosphine)$_2PdCl_2$, (triphenylphosphine)$_2PdCl_2$, tetrakis(triphenylphosphite)$Pd(O)$, tetrakis-(triethylphosphite)$Pd(O)$ and tetrakis(triphenylphosphine)$Pd(O)$. The same salts or complexes of rhodium can also be utilized.

In accordance with another aspect of this invention, we have discovered that catalytic isomerization occurs in very high yields, without the necessity of recycling with a catalyst formed by reacting palladium (II) salt with a tri(lower alkyl) or a tri(aryl phosphine), preferably a tri(aryl phosphine), in the presence of a tri(lower alkyl)amine base in an inert organic solvent, preferably acetonitrile. The presence of a tri(lower alkyl)amine improves the catalyst utilized and consequently the yield obtained by the isomerization reaction.

In accordance with this invention, for best results it is preferred that the palladium salt be palladium (II) nitrate. The preferred triarylphosphine is triphenylphosphine. Any conventional lower alkyl amine can be utilized in forming the complex with the preferred lower alkyl amine being triethylamine.

In accordance with the preferred embodiment of this invention the palladium (II) nitrate and the triaryl phosphine are dissolved in acetonitrile. To the solution of acetonitrile, there is added the tri(lower alkyl)amine. Upon the addition of the tri(lower alkyl)amine, the catalyst forms as a precipitate in the acetonitrile solution. If desired, the precipitate can be filtered from the solution and used in isomerizing the compound of formula III, either alone or in admixture with the compound of formula IV, to the compound of formula IV. On the other hand, the solution and the precipitate can be added to this substrate. In preparing the preferred catalyst, 1 mol of palladium (II) nitrate is reacted with at least 4 mols of the triarylphosphine. In carrying out this reaction, any amount in excess with the 4 mols of the triphenylphosphine per mol of palladium (II) nitrate can be utilized. However, since there is no benefit to utilizing large excesses of triphenylphosphine, molar amounts of more than 10 mols of triphenylphosphine per mol of the palladium salt are seldom used. In carrying out the reaction between triphenylphosphine and palladium (II) nitrate, any conventional solvent for triphenylphosphine and palladium (II) nitrate can be utilized. However, best results are achieved when acetonitrile is utilized as the solvent. In accordance with this invention, when a tri(lower alkyl)amine such as triethyl amine is utilized in forming the catalyst, generally at least 2 mols of triethyl amine are utilized per mol of the palladium salt or complex. If desired, the tri(lower alkyl)amine can be utilized in greater amounts such as 20 mols per mol of the palladium salt or complex. However little, if any, additional benefit results from utilizing such large amounts.

In carrying out isomerization reaction, the catalyst is present in catalytic quantity. Generally, this isomerization reaction is carried out in an inert organic solvent. Any conventional inert organic solvent can be utilized in carrying out this reaction. Among the preferred solvents are included ethers, such as tetrahydrofuran; nitriles, such as acetonitrile, and lower alkyl esters of lower alkanoic acids such as ethyl acetate. Among the preferred solvents are the lower alkyl esters of a lower alkanoic acid wherein the lower alkanoic acid contains from 2 to 4 carbon atoms. The preferred esters of lower alkanoic acid which is utilized as a solvent is ethyl acetate. In this reaction, the palladium catalyst is present in catalytic amounts. Generally, it is preferred to have the catalyst present in an amount of from about 0.0001 mols to about 0.01 mols per mole of the 11,13-dicis vitamin A acid to be isomerized. Excess amount of the catalyst can be utilized in an amount of about 1 mol per mol of the 11,13-dicis retinoic acid to be isomerized. However, in view of the fact that no additional beneficial results are achieved by utilizing large amounts of catalysts and these catalysts are costly, large amounts of catalysts are seldom utilized. Generally, it is preferred to utilize about 0.001 mols to about 0.01 mols of the catalyst per mol of the 11,13-dicis retinoic acid to be isomerized.

After the isomerization has been completed, 13-cis-retinoic acid compound of formula IV can be recovered in pure form from the reaction mixture in high yields by conventional methods such as crystallization. This crystallization can be carried out by addition of water to the reaction mixture to form a suspension and thereafter cooling the suspension to a temperature of from 0° to −5° C. This invention is further illustrated by the following Examples. The Examples are illustrative but not limitative of the claimed invention:

EXAMPLE 1

A stirred solution of

| | |
|---|---|
| 257.5 g | of [3-methyl-5-(2,6,6-trimethyl-1-cyclohexen-1-yl)-2,4-pentadienyl]-triphenylphosphonium chloride [the Wittig salt] of (0.515 mol; 1.03 equivalent based on the furanone) and |
| 57.0 g | of the butenolide, 5-hydroxy-4-methyl-2(5H)-furanone (0.500 mol) in |
| 1,000 ml. | of isopropanol was cooled to −30° C. under a nitrogen atmosphere. To the solution, |
| 625 ml. | of 2.0 N aqueous potassium hydroxide in isopropanol (1.25 mol) was added at −30° C. ± 2° C. over 1 to 1.5 hours. When the addition was completed, the reaction was stirred for 10 minutes and poured into |
| 2,500 ml. | of water. The alkaline (pH ~ 10) solution was extracted with |
| 2 × 500 ml. | of hexane. The combined hexane extracts were washed with |
| 2 × 100 ml. | of methanol-water (7:3 parts by volume), and the washes were added to the original aqueous solution. The entire aqueous solution was acidified by careful addition of |
| 250 ml. | of 4N aqueous sulfuric acid (pH ~ 2), and extracted with |
| 2,000 ml. | and |
| 2 × 1,000 ml. | of ethyl acetate-hexane (2:8 parts by volume). The ethyl acetate-hexane extracts were kept separate and each was washed in succession with the same |
| 6 × 400 ml. | of methanol-water (7:3 parts by volume). Each methanol-water wash was extracted in succession with the same |
| 3 × 1,000 ml. | of ethyl acetate-hexane (2:8 parts by volume) before the next. The end result was a total of: 6 organic (ethyl acetate-hexane) extracts 6 aqueous (methanol-water) extracts TLC analysis shows all of the triphenylphosphine oxide to be in the aqueous phases and the 11,13-dicis-retinoic acid and 16.7% by weight of 13-cis-retinoic acid to be in the organic phases. The organic extracts were combined and washed with |

| 7 × 500 ml. | of water. The solvent was evaporated to give 137.2 g. (91.5%) by weight yield of a crystalline mixture of contain 75.9% by weight of 11,13-dicis-retinoic acid and 16.7% by weight of 13-cis-retinoic acid. |

EXAMPLES 2–35

In Examples 2 to 35, the Wittig salt and the butenolide were reacted by the procedure of Example 1 to produce a crystalline mixture of 11,13-dicis-retinoic acid and 13-cis-retinoic acid. In Examples 2 to 35, the effect upon the yield of the above crystalline mixture through utilizing different temperatures for carrying out the reaction of the butenolide and Wittig salt is noted in the following Table. The % yield is given on a weight basis. The in the Table, the "scale" is the moles of butenolide used. In Examples 2–23 and 26–35, the mole ratio of butenolide to Wittig salt was kept the same as in Example 1. Therefore, if the moles of butenolide was increased from that of Examples 1, the moles of the Wittig salt was also increased to give the same mole ratio as in Example 1. In Example 24, a 10% molar excess of the Wittig salt from that of Example 1 was used. In Example 25, a 20% molar excess of the Wittig salt from that of Example 1 was used. The result of these Examples are given in Table I.

TABLE 1

| Example No. | Scale | Temp. (°C.) | % Yield |
|---|---|---|---|
| 2 | 0.02 | 0 | 61.5 |
| 3 | 0.02 | 0 | 60.0 |
| 4 | 0.02 | −20 | 91.7 |
| 5 | 0.02 | 0 | 55.0 |
| 6 | 0.02 | −20 | 81.7 |
| 7 | 0.1 | −20 | 90.0 |
| 8 | 0.1 | −20 | 88.7 |
| 9 | 0.1 | −20 | 84.7 |
| 10 | 0.1 | −10 | 80.7 |
| 11 | 0.1 | −20 | 91.0 |
| 12 | 0.1 | −10 | 82.3 |
| 13 | 0.1 | −30 | 93.7 |
| 14 | 0.1 | −30 | 99.3 |
| 15 | 0.1 | −20 | 86.0 |
| 16 | 0.1 | −30 | 98.3 |
| 17 | 0.1 | −30 | 95.0 |
| 18 | 0.1 | −30 | 95.7 |
| 19 | 0.1 | −30 | 96.7 |
| 20 | 0.1 | −30 | 92.3 |
| 21 | 0.1 | −30 | 98.7 |
| 22 | 0.1 | −30 | 99.3 |
| 23 | 0.1 | −30 | 92.3 |
| 24 | 0.1 | −20 | 93.3 |
| 25 | 0.1 | 0 | 91.3 |
| 26 | 0.1 | −20 | 62.0 |
| 27 | 0.5 | −25 | 88.3 |
| 28 | 0.5 | −30 | 91.5 |
| 29 | 0.5 | −20 | 90.0 |
| 30 | 0.5 | −30 | 91.7 |
| 31 | 0.5 | −30 | 90.7 |
| 32 | 0.5 | −30 | 89.6 |
| 33 | 0.5 | −30 | 93.5 |
| 34 | 0.5 | −30 | 93.1 |
| 35 | 0.5 | −30 | 93.2 |

EXAMPLE 37

Preparation of 13-cis-Retinoic Acid

A rapidly stirred solution of

| 137.2 g. | of the crystalline mixture of retinoic acid isomers prepared in Example 1;0.46 mol) in |
| 250 ml. | of tetrahydrofuran and |
| 500 ml. | of acetonitrile was warmed to 50° C. under a nitrogen atmosphere. A mixture of |
| 111 mg. | of palladium (II) nitrate (0.48 mmol; 0.10 mol %), |
| 509 mg. | of triphenylphosphine (1.94 mol; 4 equivalents based on palladium nitrate), and |
| 135 l | of triethylamine (98 mg; 0.097 mmol; 2 equivalents based on palladium nitrate) in |
| 25 ml. | of acetonitrile was added in one portion, followed by a rinse of |
| 25 ml. | of acetonitrile. The mixture was stirred at 50° C. for 1 hour. Immediately upon the addition of the catalyst, the reaction solution darkened. Within 1 minute, initial crystallization occurred. Within 2 minutes, a thick orange suspension resulted. The resulting orange suspension was cooled while adding |
| 500 ml. | of water. The suspension was held at 0 to +5° C. for 2 hours and filtered. The crystals were washed with |
| 4 × 100 ml. | of cold acetonitrile-water (25:75 parts by volume) and dried at room temperature under vacuum to give 128.5 g of 13-cis-retinoic acid (93.7% mol; 85.7% by weight overall based on the butenolide). |

EXAMPLES 38–43

In Examples 38 through 43, the crystalline mixture of Example 1 containing 75.9% by weight 11,13-dicis-retinoic acid and 16.7% by weight 13-cis-retinoic acid was converted to 13-cis-retinoic acid by the procedure of Example 37 using catalysts other than palladium nitrate and triphenylphosphine. In Examples 38 through 43, the same conditions except that all of the reactions were run for 3 hours at 50° C. using 0.1 mol % of catalyst with 2 equivalents of triethylamine, based upon catalyst. Isolation of the first 13-cis-retinoic acid was accomplished by the addition of excess water (final solvent content 62.5% by volume) and filtration. The % recovery given in Table 2 is % by weight of the 13-cis-retinoic acid produced based upon the weight of the crystalline mixture used as the starting material.

TABLE 2

| | Comparison of Catalysts for the Isomerization of Crude Retinoic Acid | | | |
|---|---|---|---|---|
| Example No | Catalyst | % Recovery | 13-cis | Assay all-trans | 11,13-dicis |
| 38 | (PhCN)$_2$PdCl$_2$ | 97.0 | 90.3 | 4.5 | — |
| 39 | (Ph$_3$P)$_3$RhCl | 97.3 | 58.1 | 1.8 | 35.1 |
| 40 | (Ph$_3$P)$_2$PdCl$_2$ | 98.0 | 20.6 | — | 74.5 |
| 41 | (Ph$_3$P)RhH(CO) | 98.0 | 66.6 | 1.1 | 27.3 |
| 42 | Pd(NO$_3$)$_2$ + Ph$_3$P | 97.3 | 91.0 | 0.6 | 4.1 |
| 43 | (Ph$_3$P)$_3$RuCl$_2$ | 93.3 | 15.4 | — | 78.9 |

EXAMPLES 44–53

In Examples 44 through 53, the procedure of Example 37 was followed to convert the crystalline mixture of retinoic acids produced in Example 1 to 13-cis retinoic acid utilizes different amounts of catalyst (palladium (II) nitrate). The procedure of Example 37 was carried out except as indicated below.

TABLE 3

Isomerization of Crude Retinoic Acid

| Example No. | Scale[a] | Catalyst Mol. % | Time, Minutes | Yield (%)[b] | Overall Yield (%)[c] | Assay[d] |
|---|---|---|---|---|---|---|
| 44 | 0.1 | 0.047 | 30 | 78.1 | 70.3 | 97.2 |
| 45 | 0.1 | 0.074 | 30 | 83.6 | 78.3 | 94.0[d] |
| 46′ | 0.1 | 0.043 | 30 | 91.4 | 85.3 | — |
| 47 | 0.1 | 0.070 | 150 | 78.5 | 78.0 | — |
| 48 | 0.1 | 0.046 | 180 | 84.4 | 83.0 | 97.0[e] |
| 49 | 0.1 | 0.10 | 30 | 86.8 | 81.0 | — |
| 50 | 0.5 | 0.10 | 60 | 93.1 | 82.3 | 92.7 |
| 51 | 0.5 | 0.10 | 60 | 93.7 | 85.7 | 100.5 |
| 52 | 0.5 | 0.10 | 60 | 94.2 | 84.8 | 99.4[f] |
| 53 | 0.5 | 0.10 | 60 | 94.5 | 86.7 | 99.8[g] |

[a]Scale defined as the number of moles of butenolide used in Example 1.
[b]Wt. % recovery from crystalline mixture of retinoic acid.
[c]Overall % yield based on butenolide (uncorrected).
[d]Product contained 1.4% of 11,13-dicis-retinoic acid.
[e]Product contained 0.8% of 11,13-dicis-retinoic acid.
[f]Product contained 0.7% all-trans and 0.5% of 11,13-dicis-retinoic acid.
[g]Product contained 0.7% of 11,13-dicis-retinoic acid.

EXAMPLE 54

All operations were performed under nitrogen. To a 50-gal., stainless-steel, turbine-agitated, dry ice-acetone-cooled reactor,

| | |
|---|---|
| 34.3 kg. (43.8 L., 11.6 gal.) | of isopropanol, |
| 5.0 kg. | of the $C_5$-butenolide, 5-hydroxy-4-methyl-2-5(H)-furanone, and |
| 23.0 kg. | of the $C_{15}$-Wittig salt, [3-methyl-5(2,6,6-trimethyl-1-cyclohexen-1-yl)-2,4-pentadienyl]-triphenylphosphonium chloride were charged. This mixture was agitated to effect solution, cooled to −22 to −25° C., and maintained at this temperature. To this batch there was added |
| 49.9 kg. | of 2.0 N potassium hydroxide-isopropanol solution (at +5 to +10° C.) over a period of ca. 1.5 hours at −22 to −25° C. When the addition was completed, the batch was agitated for an additional 1 hour at −22 to −25° C. To a 100-gal., glass-lined quench kettle, there was charged |
| 151.4 kg. (40.0 gal.) | of deionized water and |
| 54.6 kg. (87.8 L., 23.2 gal.) | of hexane. |

The batch was dropped from the 50-gal. reactor to the quench kettle with agitation at room temperature. The mixture was agitated for 10 minutes, allowed to settle, and the lower layer (containing the batch) was separated. The hexane layer was extracted with a mixture of

| | |
|---|---|
| 4.8 kg. (6.1 L., 1.6 gal.) | of methanol and |
| 2.6 kg. (0.7 gal.) | of deionized water. |

The methanol-water back-extract and the batch was transferred to a 500-gal., glass-lined, brine-cooled reactor. This solution was held at 0° to +10° C. under nitrogen. The above procedure was repeated three times for a total of four reactions (4 × 5.0 or 20.0 kg. of $C_5$-butenolide consumed). The four batches were combined in the 500-gal. reactor. The combined batches were acidified to a pH of 4.0 to 4.5 by the careful addition of

| | |
|---|---|
| 32.5–35.6 kg. | of 85% by weight aqueous phosphoric acid. The resulting batch was extracted with a mixture of |
| 115.8 kg. (128.7 L., 34.0 gal.) | of ethyl acetate and |
| 343.9 kg. (514.8 L., 136.0 gal.) | of hexane. [Extract #1]. |

Extract #1 was washed with

| | |
|---|---|
| 94.6 kg. (25.0 gal.) | of deionized water. After washing, the spent aqueous layer and the water wash were discarded. Extract #1 was then washed with six portions of mixture of |
| 54.4 kg. (68.7 L., 18.1 gal.) | of methanol and |
| 29.5 kg. (7.8 gal.) | of deionized water-Washes #1-6. Each of Washes #1-6 were extracted in succession with five portions of a mixture of |
| 44.2 kg (49.1 L., 13.0 gal.) | of ethyl acetate and |
| 131.3 kg. (196.5 L., | of hexane-Extracts #2-6. |

| | |
|---|---|
| 51.9 gal.) | |
| | When all of the extractions and washes were completed, the ethyl acetate-hexane Extracts #1-6 were combined and concentrated by vacuum distillation at 50-100 mmHg and a batch temperature of 20-30° C. to a final volume of ca. 150 gal.<br>The vacuum under nitrogen was released and charcoal was added. |
| 2.0 kg. | The batch was agitated with charcoal for 30 minutes at 20 to 25° C. and filtered through a filter coated with diatomaceous earth into a 200-gal., glass-lined, tempered-brine reactor. The first reactor and filter cake were rinsed with |
| 34.1 kg.<br>(37.9 L.,<br>10.0 gal.) | of ethyl acetate and this rinse was added to the batch in |
| | the 200-gal. reactor. The batch was concentrated by vacuum distillation as before to a final volume of 25 gal. The batch was added to |
| 34.1 kg.<br>(37.9 L,<br>10.0 gal.) | of ethyl acetate and again concentrated to a final volume of 25 gal. |
| | The temperature of the batch was adjusted to 50° C. To the batch there was added a solution of |
| 2.65 kg.<br>(3.37 L.) | of acetonitrile, containing |
| 33.7 g. | of palladium (II) nitrate, |
| 162.4 g. | of triphenylphosphine, and |
| 31.8 g. | of triethylamine.<br>This solution was added to the batch with an additional |
| 1.0 L. | of ethyl acetate. The batch was agitated at 50° C. for 1 hour, cooled to −10 to −15° C. over a 2-hour period, and held at this temperature overnight. The crystals of crude 13-cis-retinoic acid were filtered and spray-washed with |
| 3 × 10.2 kg.<br>(3 × 11.4 L.,<br>3.0 gal.) | of ethyl acetate at −10 to −15° C. |
| | The crystals were spun as dry as possible in the centrifuge.<br>To a 100-gal., glass-lined, steam-heated dissolver were charged in two-parts |
| 356.4 kg.<br>(396.0 L.,<br>104.6 gal.) | of ethyl acetate, |
| 39.7 kg. | of ethyl acetate wet 13-cis-retinoic acid prepared above and |
| 2.0 kg. | of charcoal.<br>The batch was heated to reflux (75-80° C.) to dissolve the crystals of crude 13-cis-retinoic acid and the mixture was agitated at relux for 30 minutes. The solution was clarified by filtration through a pressure filter coated with diatomaceous earth into a 200-gal., glass-lined, tempered-brine crystallizer. The dissolver and pressure filter were rinsed with |
| 68.1 kg.<br>(75.7 L.,<br>20.0 gal.) | of ethyl acetate and this rinse was added |
| | to the batch in the crystallizer.<br>The batch was concentrated by distillation under an atmosphere of nitrogen (pot temperature of 75-80° C.) to a final volume of 30 gal. The batch was cooled to −10 to −15° C. and that temperature was maintained overnight.<br>The crystals of pure 13-cis-retinoic acid were filtered and spray-washed with three portions of |
| 10.2 kg.<br>(11.4 L.,<br>3.0 gal.) | of ethyl acetate at −10° to −15-C. |
| | The crystals were dried for 24 hours at 50-100 mmHg and 35° C. with a slight purge of nitrogen. |

EXAMPLE 55

To a 2000 ml jacketed resin flask equipped with a stirrer, a low temperature thermometer, and a dropping funnel,

| | |
|---|---|
| 262.5 g | $C_{15}$-Wittig salt (0.525 mol), |
| 57.0 g | $C_5$-butenolide (0.500 mol), and |
| 1000 ml | isopropanol was added under a nitrogen atmosphere. The resulting solution was cooled to −25° C. and |
| 625 ml. | 2.0N potassium hydroxide-isopropanol (1.25 mol) was added over a one hour period of −20 to −25° C. When the addition was complete, the mixture was stirred for an additional one hour at −25° C. and then was poured into |
| 2500 ml | of deionized water. The resulting mixture was extracted with |

-continued

| | |
|---|---|
| 2 × 500 ml | hexane (to remove non-polar impurities). The combined hexane layers were washed with |
| 2 × 100 ml | methanol-water(70%–30% v/v). The hexane extracts were concentrated to give 9.8 g of a yellow oil which was discarded. The combined aqueous layers were carefully adjusted to pH 4 by the addition of |
| 55 ml | 85% phosphoric acid. The resulting suspension was extracted with |
| 2000 ml | of ethyl acetate-hexane (20%–80% v/v). This extract was washed sequentially with |
| 6 × 400 ml | methanol-water (70%–30% v/v). Each wash was held separate and back-extracted sequentially with |
| 5 × 1000 ml | ethyl acetate-hexane (20%–80% v/v). After all of the extractions were completed, the six ethyl acetate-hexane extracts were combined, washed with |
| 2 × 500 ml | deionized water, and concentrated under vacuum to give 130.4 g (86.9% yield) of a crystalline mixture containing about 70–85% by weight 11,13-dicis-retinoic acid and about 15–30% by weight 13-cis-retinoic acid. |

EXAMPLE 56

Isomerization of Crude Retinoic Acid; Preparation of 13-cis-Retinoic Acid

To a 1000 ml jacketed resin flask equipped with a stirrer, a condenser, and a thermometer,

| | |
|---|---|
| 130.4 g | of the crystalline mixture prepared in Example 55 (0.434 mol) and |
| 200 ml | ethyl acetate were added. The resulting solution was stirred at 50° C. under a nitrogen atmosphere and a mixture of |
| 100 mg | palladium (II) nitrate (0.434 mmol; 0.1 mol %), |
| 482 mg | triphenylphosphine (1.84 mmol), |
| 94.4 mg | triethylamine (0.934 mmol), and |
| 25 ml | acetonitrile was added. The reaction solution immediately darkened and crystallized to a thick orange suspension in one minute. The mixture was stirred at 50° C. for one hour, cooled to −10° to −15° C. for two hours, filtered on a funnel, washed with |
| 3 × 50 ml | of cold ethyl acetate and dried in vacuo to give 117.7 g of pure 13-cis vitamin A acid (90.3% yield of the crystalline mixture prepared in Example 55; 78.4% overall from C5-butenolide) |

EXAMPLE 57

Isolation of Pure 11,13-dicis-Retinoic Acid

A batch of the crystalline mixture of 13-cis retinoic acid and 11,13-dicis retinoic acid as in Example 55 weighing

| | |
|---|---|
| 121.2 g | was dissolved in |
| 500 ml. | diethyl ether. This solution was concentrated by the distillation of |
| 250 ml | ether while replacing with an equal volume of hexane. An additional |
| 250 ml | hexane was added and the resulting solution was allowed to cool to room temperature undisturbed for about four hours. (If the solution was allowed to stand overnight, dark orange crystals of 13-cis-retinoic acid were deposited on the surface of the yellow crystals of 11,13-dicis-retinoic acid). The crystals were filtered, washed with |
| 3 × 100 ml | of cold hexane, and dried in vacuo at room temperature. Three such batches of 11,13-dicis-retinoic acid were combined and the above recrystallization procedure was repeated twice for a total of three recrystallizations from ether-hexane. This gave 74.6 g of crystalline 11,13-dicis-retinoic acid. |
| 74.6 g | of 11,13-dicis-retinoic acid from the ether-hexane recrystallizations was dissolved in |
| 250 ml | ethyl acetate with warming and the warm solution (55–60° C.) was filtered through diatomaceous earth to remove foreign matter. The filter cake was washed with |
| 2 × 100 ml | of hot (70–75° C.) ethyl acetate. The combined filtrate and washes were concentrated to a final volume of |
| ca 200 ml | and allowed to cool as before. The crystals which formed were filtered, washed with |
| 2 × 100 ml | of cold ethyl acetate and dried in vacuo to give 39.3 g of pure 11,13-dicis-retinoic acid, mp 124.5–126.0° C. |

EXAMPLE 58

Preparation of 13-cis-Retinoic Acid from 11,13-dicis-Retinoic Acid

To a 100 ml flask under a nitrogen atmosphere

| | |
|---|---|
| 8.0 g | of 11,13-dicis-retinoic acid (26.6 mmol) and |
| 25 ml | of ethyl acetate were added. To the resulting solution, at 50° C., a mixture of |
| 10.0 mg | of palladium(II)nitrate (0.434 mmol), |
| 60.0 mg | of triphenylphosphine (0.229 mmol), |
| 9.4 mg | of triethylamine (0.093 mmol), and |
| 2.5 ml | of acetonitrile was added. Crystallization occurred within 3–5 minutes. The mixture was stirred at 50° C. for 1 hour, cooled to -10° C., and filtered. The crystals were washed with |
| 3 × 20 ml | of cold (−20° C.) ethylacetate and dried in vacuo to give 7.28 g (91.5%) of 13-cis-retinoic acid. |

I claim:

1. A process for producing the 13-cis isomer of the formula:

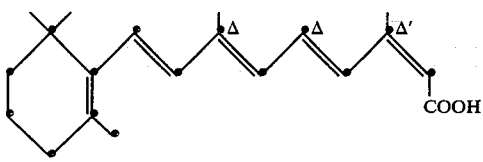

wherein the Δ indicates the trans configuration about the double bond; and Δ' indicates the cis configuration about the double bond;
comprising
(a) reacting in a lower alkanol solvent in the presence of an alkali metal hydroxide, a butenolide of the formula:

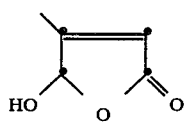

with a salt of the formula:

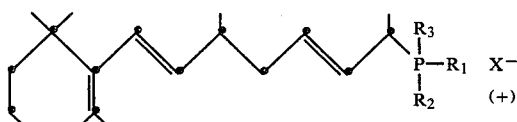

wherein $R_1$, $R_2$ and $R_3$ are aryl or di(lower alkyl)amino, and X is halogen;
said reaction being carried out at a temperature of from −10° to −50° C.; and
(b) forming said 13-cis isomer by contacting the reaction product of step (a) in an organic solvent medium with a catalyst, said catalyst comprising a triaryl or trialkyl phosphine and a compound or chelate of rhodium or palladium other than palladium or rhodium phthalocyanine or a palladium or rhodium compound containing a cyanide ion.

2. The process of claim 1 wherein said reaction is carried out at −30° C. to −45° C.

3. The process of claim 1 wherein said catalyst is formed by reacting, in a solvent, medium palladium (II) nitrate with a triaryl or trialkylphosphine in the presence of a lower alkyl amine.

4. The process of claim 3 wherein said phosphine is triphenylphosphine and the amine is diethylamine.

5. The process of claim 4 wherein said solvent medium for forming the catalyst is acetonitrile.

6. A process for preparing the 13-cis isomer of the formula:

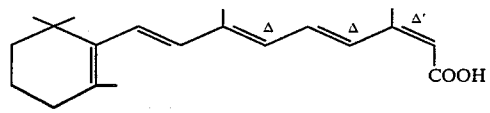

wherein the Δ indicates the trans configuration about the double bond and the Δ' indicates the cis configuration about the double bond;
comprising contacting a dicis compound of the formula:

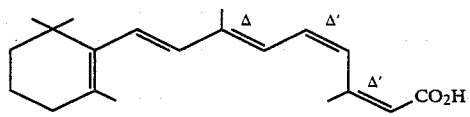

wherein Δ and Δ' are as above, in an inert organic solvent medium containing an inert organic solvent and a solid catalyst, said catalyst being formed in said solvent by reacting one mole of a palladium (II) salt other than palladium (II) cyanide or palladium (II) phthalocyanin with at least four moles of a triarylphosphine, and being precipitated from said solvent by adding at least four moles of a tri(-lower alkyl)amine per mole of said palladium (II) salt utilized to form said catalyst.

7. The process of claim 6 wherein said palladium (II) salt is palladium nitrite and said phosphine is triphenyl phosphine.

8. The process of claim 7 wherein said solvent is acetonitrile.

9. The process of claim 8 wherein said amine is triethylamine.

10. A process for preparing the 13-cis isomer of the formula:

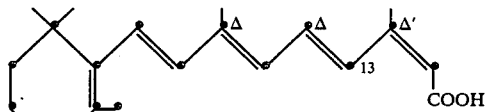

wherein the Δ indicates the trans configuration about the double bond; and Δ' indicates the cis configuration about the double bond;
comprising contacting a dicis compound of the formula:

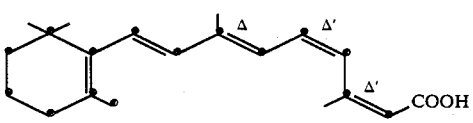

wherein Δ and Δ' is as above in an inert organic solvent medium with a catalyst to form said 13-cis isomer, said catalyst containing a compound or chelate of rhodium or palladium other than palladium or rhodium phthalocyanine or a palladium or rhodium complex or compound containing a cyanide ion and a triaryl or trialkyl phosphine.

11. The process of claim 10 wherein said catalyst is a salt or complex palladium.

12. The process of claim 11 wherein said catalyst is formed by reacting, in a solvent, medium palladium (II) nitrate with a triaryl or trialkylphosphine in the presence of a lower alkyl amine.

13. The process of claim 12 wherein said phosphine is triphenylphosphine and the amine is diethylamine.

14. The process of claim 13 wherein said solvent medium for forming the catalyst is acetonitrile.

* * * * *